United States Patent [19]
Linsley et al.

[11] Patent Number: 5,874,536
[45] Date of Patent: Feb. 23, 1999

[54] PROTEINS WITH ONCOSTATIN M ACTIVITY AND PROCESS FOR THEIR PREPARATION

[75] Inventors: Peter S. Linsley; Jeffery C. Kallestad, both of Seattle, Wash.

[73] Assignee: Bristol-Myers Squibb Company, Princeton, N.J.

[21] Appl. No.: 623,867

[22] Filed: Dec. 3, 1991

Related U.S. Application Data

[63] Continuation-in-part of Ser. No. 447,759, Dec. 8, 1989, abandoned.
[51] Int. Cl.[6] .............................. C07K 1/00; C07K 14/00; C07K 17/00; A61K 38/00
[52] U.S. Cl. ............................................. 530/351; 530/350
[58] Field of Search ................................................ 530/350

[56] References Cited

FOREIGN PATENT DOCUMENTS 0290948  11/1988  European Pat. Off. ........ C12N 15/00

OTHER PUBLICATIONS

Zarling et al., 1986, Proc. Natl. Acad. Sci. USA 83:9739–9743.
Brown et al., 1987, J. Immunol. 134:2977–2483.
European Patent Application 0290948, published Nov. 17, 1988.
Linsley et al., 1989, J. Biol. Chem. 264:4282–4289.
Malik et al., 1989, Mol. Cell. Biol. 9:2847–2853.

Primary Examiner—Lynette F. Smith
Attorney, Agent, or Firm—Pennie & Edmonds LLP

[57] ABSTRACT

The present invention is directed to biologically mutant forms of the cell growth regulatory factor Oncostatin M. The Oncostatin M mutants of the invention comprise deletion, substitution and insertion mutants and may be prepared using recombinant DNA, in vitro mutagenesis and heterologous expression techniques. Oncostatin M mutants may be useful in eliciting Oncostatin M biological responses and, as such, may find a variety of therapeutic uses including but not limited to the treatment of neoplasias.

12 Claims, 3 Drawing Sheets

PROTEINS WITH ONCOSTATIN M ACTIVITY AND PROCESS FOR THEIR PREPARATION

This application is a continuation-in-part of application Ser. No. 07/447,759, filed Dec. 8, 1989, now abandoned, which is incorported by reference herein in its entirety.

TABLE OF CONTENTS

1 Introduction
2 Background of the Invention
3 Summary of the Invention
4 Brief Description
5 Detailed Description
   5.1 Uses of Oncostatin M Mutant and Analogs
6 Example: Expression and Characterization Of Oncostatin M Mutants
   6.1 Materials and Methods
      6.1.1 Cell Culture
      6.1.2 Growth Inhibition Assay
      6.1.3 Radioreceptor Assay
      6.1.4 Radioimmunoassay
      6.1.5 Antisera
      6.1.6 COS Cell Transfections
   6.2 Construction of Expression Plasmids
      6.2.1 Deletion Mutant Constructs
      6.2.2 Processing Mutants Constructs
      6.2.3 Substitution Mutant Constructs
      6.2.4 Insertion Mutants Constructs
   6.3 Bioactivity of Oncostatin M Mutants
      6.3.1 Deletion and Processing Mutants
      6.3.2 Substitution Mutants
      6.3.3 Oncostatin M Mutations Involving Deletions and Insertions of Amino Acids
7 Example: Expression of Oncostatin M In COS Cells Generates Two Molecular Forms
   7.1 COS Transfections
   7.2 Purification of the $M_r$32,000 Form of Oncostatin M
   7.3 $M_r$36,000 Forms
   7.4 Electrophoresis
   7.5 Trypsin Treament of $M_r$36,000 Oncostatin M
   7.6 Removal of Oligosaccharides
   7.7 Site-Specific Antisera Reveal Different C-Termini For The $M_r$36,000 And $M_r$32,000 Forms of Oncostatin M
   7.8 Conversion of The M r36,000 Form Of Oncostatin M To The $M_r$32,000 Form By Limited Proteolysis
   7.9 Growth Inhibitory Activity of Oncostatin M (32K and 36K Forms)

1. INTRODUCTION

The present invention is directed to Oncostatin M mutants and analogs having Oncostatin M bioactivity, including deletion, substitution, insertion and processing mutants. The Oncostatin M mutants of the invention may be useful in eliciting Oncostatin M-induced biological responses to a greater or lesser extent than native Oncostatin M. The invention is described by way of examples in which a variety of Oncostatin M mutants are prepared and characterized.

2. BACKGROUND OF THE INVENTION

Oncostatin M, originally identified for its inhibitory effects on human tumor cell lines, was first isolated from phorbol 12-myristate 13-acetate (PMA)-induced human histiocytic lymphoma cells (Zarling et al., 1986, Proc. Natl. Acad. Sci. USA 83: 9739–9743) and from activated T lymphocytes (Brown et al., 1987, J. Immunol. 139: 2977–2983). The molecule is a heat and acid stable protein comprised of a single polypeptide chain $M_r$=28,000. Like other naturally occurring growth regulators, Oncostatin M exhibits a variety of biological activities. Growth inhibition is observed with some, but not all, human tumor cell lines. In contrast, the growth of some normal fibroblasts, such as human foreskin fibroblasts or WI-38 cells, is stimulated by exposure to Oncostatin M (Zarling et al., 1986, Proc. Natl. Acad. Sci. USA 83: 9739–9743).

The gene for Oncostatin M has been cloned and sequenced, and an active form of recombinant Oncostatin M has recently been expressed in mammalian cells (copending U.S. Application Ser. No. 144,574 filed Jan. 15, 1988, which is incorporated herein by reference in its entirety). The mature form of Oncostatin M is a glycoprotein containing 228 amino acids, five of which are cysteine residues. The protein has an extremely hydrophilic carboxy terminal domain. Although Oncostatin M is not structurally related to other known cytokines, its mRNA contains an AU-rich region at its 3' untranslated end. This region in the Oncostatin M message is homologous to that of many cytokines, lymphokines and other growth-regulatory moelcules, suggesting a common mode of regulating gene expression. A cellular receptor for Oncostatin M has been found on a variety of mammalian cells. The major Oncostatin M receptor molecule is a specific protein of $M_r$=150,000–160,000 (Linsley et al., 1989, J. Biol. Chem. 264: 6528 –6532).

3. SUMMARY OF THE INVENTION

The present invention is directed to novel compositions comprising deletion, processing, insertion and/or substitution mutants of Oncostatin M, as well as derivatives and fragments thereof. The invention also relates to the expression of Oncostatin M mutants in recombinant systems. Also provided are compositions having the secondary structure of the Oncostatin M binding region which are capable of binding specifically to the Oncostatin M receptor. Oncostatin M mutants may be prepared by transforming a host cell with an expression vector comprising a DNA sequence encoding the desired Oncostatin M mutant polypeptide, growing the transformed host cell to express the exogenous DNA sequence, and recovering the resultant Oncostatin M mutant polypeptide from a cell lysate or from conditioned growth medium. The Oncostatin M mutant polypeptides may have altered biological activity compared to natural Oncostatin M, particularly growth inhibitory activity. The compositions of the invention may be useful, inter alia, in modulating neoplastic cell proliferation.

5. DETAILED DESCRIPTION OF THE INVENTION

The present invention is directed to Oncostatin M mutants which retain Oncostatin M bioactivity. The invention is based in part upon the elucidation of essential Oncostatin M functional domains and the discovery that certain mutations not only preserve but, in some instances, significantly enhance biological activity. The invention is illustrated by way of examples in which various deletion, processing, insertion and substitution mutant Oncostatin M polypeptides are prepared and characterized using recombinant DNA mutagenesis and expression techniques.

In a specific embodiment, Oncostatin M deletion mutants from which part or all of the carboxy-terminal 42 amino acids of native Oncostatin have been removed are prepared. Any of the amino acids from and including the residue at position 186 to and including the carboxy-terminal residue position 227 in the structure of Oncostatin M (FIG. 1) may be deleted to yield biologically active Oncostatin M mutants. Not only do these Oncostatin M deletion mutants retain biological activity, but several are significantly more active than the native Oncostatin M species.

In another embodiment, Oncostatin M substitution mutants in which at least one of the cysteine residues of native Oncostatin M are replaced by an amino acid other than cysteine, preferably serine, are prepared. Applicants substituion mutagenesis studies have revealed that of the two disulfide linkages present in the native Oncostatin M secondary structure, only the one between cysteine residues 49 and 167 is required for Oncostatin M bioactivity. Therefore, since eliminating the disulfide linkage between the cysteines at residue postions 6 and 127 is not functionally disabling, Oncostatin M mutants incapable of forming that disulfide linkage are nevertheless biologically active and functional growth modulating polypeptides. As is described more fully in the examples which follow, such bioactive Oncostatin M substituion mutants may be prepared by replacing either or both of the cysteine residues which participate in this "non-essential" disulfide linkage. In addition, the cysteine residue at postion 80 may be substituted without sacrificing biological activity. The Oncostatin M substitution mutants of the invention may possess advantages over native Oncostatin M with respect to their preparation, formulation into pharmaceutical compositions, and/or capacity to affect a descired biological response. For example, such Oncostatin M substituion mutants may be engineered so as to minimize or indeed eliminate the possibility of disulfide bond scrambling and any resulting secondary structural distortions.

The aforementioned and other embodiments of the present invention are described by way of the following examples which are representative of applicants' investigations and discoveries respecting the preparation and use of the Oncostatin M mutants of the invention. As a consequence of these investigations and discoveries, various aspects of the Oncostatin M structure that must be or should be maintained to preserve functional integrity have been identified and should be considered when preparing the Oncostatin M mutants of the invention. In this regard, functionally important sequences exist throughout the Oncostatin M polypeptide and are not confined to a single domain. For example, scanning deletion and insertion mutagenesis identifies amino acid residues 22–36 and 44–77 to be essential for biological activity. Also, the deletion of C-terminal residues to position 186 does not destroy biological activity, but mutants lacking amino acids 185 to 182 have no activity. Other sequences important for Oncostatin M growth inhibitory and receptor binding activities include residues 118–121 and 178–181, which sequences may be essential for the correct processing and/or secretion by mammalian cells of Oncostatin M and Oncostatin M mutants, since Oncostatin M mutants lacking these sequences could not be detected. Similarly, maintaining an asparagine residue at position 71 may be necessary for full bioactivity and/or secretion from mammalian cells.

A strongly amphiphilic region occurs at the Oncostatin M C-terminus between C167 and the peptide cleavage site at R196. Substituting glycines for the phenylalanines at positions 176 and 184 destroys activity, but substituting glycines for the histidines at positions 171, 174 and 178 does not affect biological function.

A close physical association of the carboxy and amino termini may exist as suggested by the blockage of amino terminal epitopes in some but not all carboxy terminal deletion mutants.

The Oncostatin M mutants of the invention and analogs thereof may be prepared by modifying the native Oncostatin M polypeptide itself, by recombinant DNA techniques, and by chemical synthetic techniques such as solid phase peptide synthesis.

In accordance with the subject invention, novel DNA constructs and novel polypeptide compositions having at least one Oncostatin M activity are provided. The absolute amount of activity may be higher or lower than that of native Oncostatin M. The polypeptides having Oncostatin M activity include deletion mutant proteins of Oncostatin M in which at least substantially all of the C-terminal region has been deleted as well as mutant proteins having the same secondary structure as the binding site of native Oncostatin M. Plasmid constructs comprising DNA sequences encoding the desired polypeptides having Oncostatin M activity are used to transform a host cell, which is cultured to express the desired polypeptide. The transformed host cell is then grown to express the inserted DNA sequence. The host cell may be either a eukaryotic or a prokaryotic cell.

Human Oncostatin M has the following amino acid sequence:

```
                        10                              20                              30
A— A— I— G— S— C— S— K— E— Y— R— V— L— L— G— Q— L— Q— K— Q— T— D— L— M— Q— D— T— S— R— L—

40                              50                              60
L— D— P— Y— I— R— I— Q— G— L— D— V— P— K— L— R— E— H— C— R— E— R— P— G— A— F— P— S— E— E—

70                              80                              90
T— L— R— G— L— G— R— R— G— F— L— Q— T— L— N— A— T— L— G— C— V— L— H— R— L— A— D— L— E— Q—

100                             110                             120
R— L— P— K— A— Q— D— L— E— R— S— G— L— N— I— E— D— L— E— K— L— Q— M— A— R— P— N— I— L— G—

130                             140                             150
L— R— N— N— I— Y— C— M— A— Q— L— L— D— N— S— D— T— A— E— P— T— K— A— G— R— G— A— S— Q— P—
```

-continued

```
               160                            170                              180
P— T— P— T— P— A— S— D— A— F— Q— R— K— L— E— G— C— R— F— L— H— G— Y— H— R— F— M— H— S— V—

190                            200                              210
G— R— V— F— S— K— W— G— E— S— P— N— R— S— R— R— H— S— P— H— Q— A— L— R— K— G— V— R— R— T—

220           227
R— P— S— R— K— G— K— R— L— M— T— R— G— Q— L— P— R
```

Single letter abbreviations for the amino acids are used, and have the following meaning: A=alanine; R=arginine; N=asparagine; D=aspartic acid; C=cysteine; A=glutamine; E=glutamic acid; G=glycine; H=histidine; I=isoleucine; L=leucine; k=lysine; M=methionine; F=phenylalanine; P=proline S=serine; T=threonine; W=tryptophan; Y=tyrosine; and V=valine.

Oncostatin M is further characterized having a molecular weight of about 32–36 kD as determined by polyacrylamide gel elctrophoresis under reducing or non-reducing conditions. Active preparations of isolated Oncostatin M contain a mixture of high mannose and complex N-linked oligosaccharide. However, non-glycosylated preparations of Oncostatin M retain cell growth modulatory activity.

Oncostatin M is also characterized by its activity toward certain cell strains. Oncostatin M stimulates proliferation of normal human fibroblasts as exemplified by WI38 and WI26 cells and inhibits proliferation of tumor cells such as A375, HBT10, A549 and SK-MEL28 and may augment growth of colony forming cells from normal bone marrow. However, it lacks cytotoxic activity against WI26 and WI38 human fibroblasts, and mouse L929 cells which are sensitive to tumor necrosis factor, and a γ-interferon-sensitive human tumor cell line. Oncostatin M does not inhibit proliferation of normal human T-lymphocytes and does not inhibit granulocytic/myelocytic colony formation from bone marrow cells at concentrations up to 100 GIA units/ml. Further, it does not suppress human proliferative or cytotoxic T cell responses in mixed leukocyte culture reactions (MLC) at concentrations of 500 GIA units/ml. Oncostatin M is stable to moderate acid and base, and to heat treatment at 56° C.

The polypeptides of this invention include various groups of polypeptides each having a common feature, wherein the polypeptides are characterized as having at least one characteristic of Oncostatin M. The groups include the common features of being deletion mutants, processing mutants, or substitution mutants of Oncostatin M or polypeptides having the same secondary structure as the binding region of native Oncostatin M. The polypeptides may also comprise combination mutations in which a plurality of substitution, deletion, processing and/or insertion mutations are incorporated. The invention includes such Oncostatin M analogs, mutants, and functional portions thereof. The polypeptides of the invention will have at least one biologically active sequence which is, for example, immunoreactive or capable of receptor binding, where such sequence may compete with native Oncostatin M for the biological property.

The following definitions are used:

"Deletion mutants" lack all or a portion of the Oncostatin M C-terminal region.

"Substitution mutants" are Oncostatin M mutants wherein one amino acid has been substituted by another amino acid. Of particular interest are substitutions of sulfhydryl groups unnecessary for biological activity. Such mutations may include a substitution of the cysteine residue by another uncharged amino acid, such as serine, glycine, threonine and the like, having charge properties and space-filling characteristics similar to those of as cysteine, particularly serine.

"Processing mutants" are mutants in which a proteolytic cleavage site within the Oncostatin M polypeptide has been mutated so that processing of the mature polypeptide is blocked. This change may result in a molecule having altered biological activity. Examples of such processing sites include amino acid residues 195 and 196.

"Insertion mutants" are mutants in which codons encoding the amino acid sequence glycine-alanine-glycine are placed in regions of the DNA sequence believed to encode amino acids of important functional significance. Examples include insertions placed between amino acid positions 5 and 6, 76 and 77, 103 and 104, and 139 and 140.

The polypeptides of the subject invention also include polypeptides wherein the secondary structure of the binding region of the polypeptide is at least substantially the same as that of the binding region of native Oncostatin M. By "binding region" is intended the region at the C-terminus and the region at the N-terminus of native Oncostatin M which are brought into proximity by disulfide bond C49–C167 (see FIG. 1) which portion of the molecule is capable of binding specifically to an Oncostatin M receptor molecule with high affinity. The binding region is characterized as having an amphiphathic helix in the region at the C-terminus, particularly the region including amino acids 168–195. By "amphipathic helix" is intended a region having hydrophobic amino acid residues on one side and hydrophilic residues on the other. The helix generally comprises about 30% to 50%, generally about 40%, hydrophobic amino acids, for example, valine, phenlalanine, methionine, leucine and the like; about 30% to 50% hydrophilic amino acids, generally about 40%, for example, tyrosine, lysine, arginine, histidine, and the like; and about 10% to 40%, generally 20%, amino acids having at least substantially no hydrophobic or hydrophilic character, for example, serine, glycine and the like. Included are polypeptides wherein the primary structure of the polypeptide in the C-terminal region is capable of maintaining a secondary structure in an aqueous solution, particularly a physiologic salt solution or the like where the secondary structure is at least substantially similar to that of native Oncostatin M under similar conditions.

The amino acid sequence of the polypeptide may be the same as or different from that of native Oncostatin M, usually similar. Where the structure is different, substitutions may be made by substituting one hydrophobic amino acid for another, and/or one hydrophilic amino acid for another, particularly an amino acid with similar charge properties and space-filling characteristics so as to at least substantially maintain secondary structure and Oncostatin M receptor-specific binding capacity. The activity of the polypeptide bound to the Oncostatin M receptor need not be the same as that of native Oncostatin M and may be that of an agonist or of an antagonist of Oncostatin M, in whole or in part.

"Biological activity" is intended to include cell growth modulatory activity, immunological cross-reactivity with naturally occurring human Oncostatin M, or high affinity Oncostatin M receptor binding. By "cell growth modulatory activity" is meant the biological activity of naturally occurring Oncostatin M, which includes inhibition of growth of neoplastic cells and stimulation of growth of normal cells, including cells of the hematapoietic system. The cell growth modulatory activity may be different from naturally occurring Oncostatin M, usually reduced. By "biologically active sequence" is intended an amino acid sequence constituting up to the full length of the polypeptide. By "immunological cross-reactivity" is meant that an antibody induced by a novel polypeptide of this invention will bind specifically to intact Oncostatin M, at least when Oncostatin M is in a native state, and that an antibody to Oncostatin M will bind specifically to the novel peptide where Oncostatin M and the novel polypeptide have a common epitopic site.

By "Oncostatin M receptor" is meant a binding site on the surface of a cell which specifically binds Oncostatin M with high affinity, the binding being saturable and not inhibited by structurally unrelated polypeptides. By "analog" is intended compounds having at least one biological activity corresponding to that of Oncostatin M and including an amino acid sequence substantially equivalent to at least part of the amino acid sequence of Oncostatin M. Analogs may comprise more or fewer amino acids in comparison to native Oncostatin M.

Figure 1:
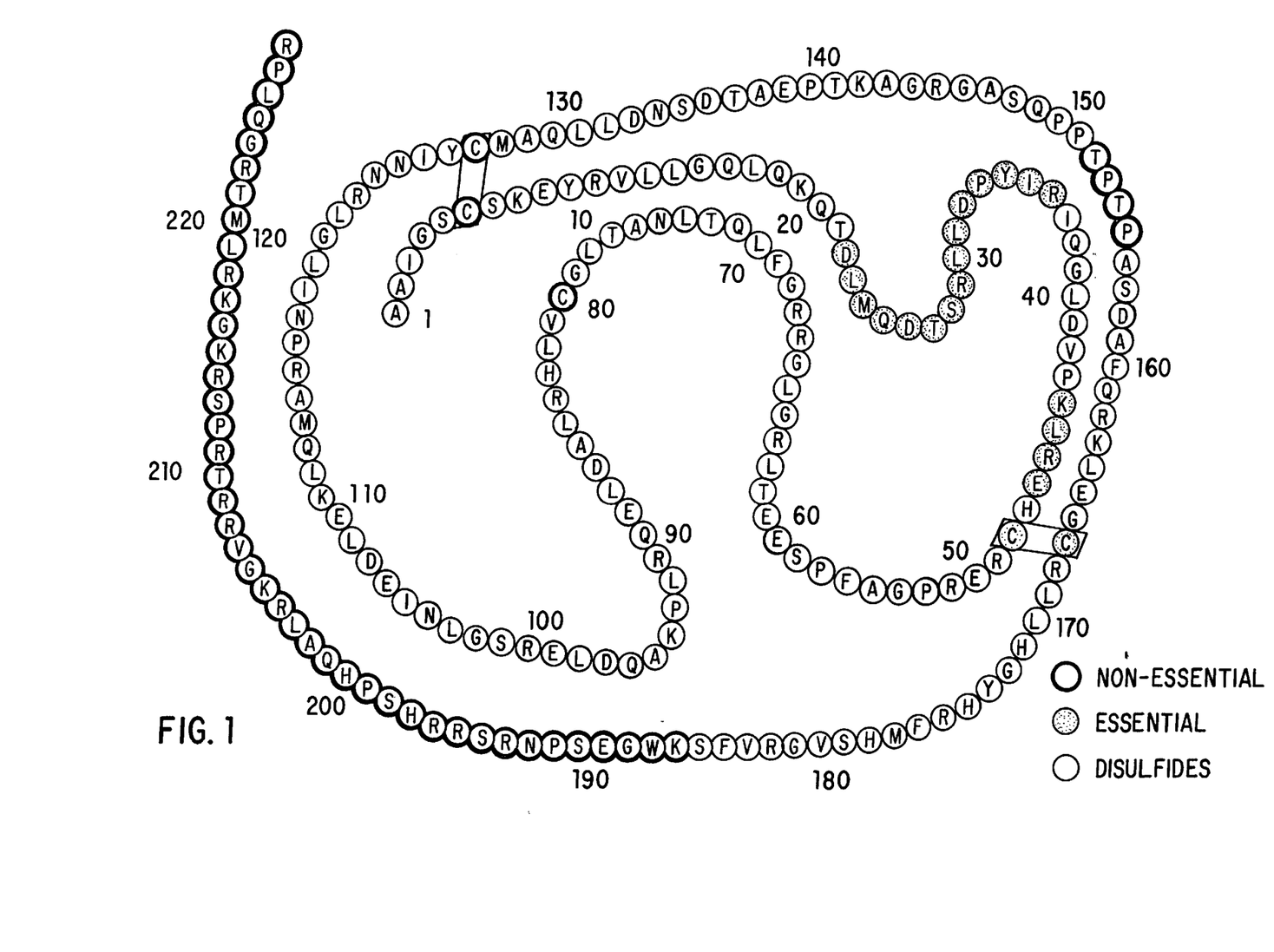
FIG. 1. Schematic representation of the amino acid sequence and functional regions of Oncostatin M. Amino acids are designated by the standard one-letter code.

The various Oncostatin M mutants and analogs may be prepared using as a starting material naturally occurring or recombinant Oncostatin M. Oncostatin M may be obtained from natural sources, particularly growth medium supplemented with an appropriate inducer such as an ingenol or phorbol and conditioned by a cell line (U937) derived from a human histiocytic lymphoma (Sundstrom and Nilsson, 1976, Int. J. Cancer 17: 565–577) or a mitogen such as phytohemoglutinen (PHA) and conditioned by normal human peripheral blood lymphocytes (PBL). Oncostatin M mutants and analogs may be purified so as to be at least substantially free of cellular components by employing various purification techniques well known in the art, including but not limited to solvent extraction, gel permeation chromatography, reversed phase-HPLC, electrophoresis, or the like. Deletion mutants of the C-terminus of Oncostatin M may be obtained by proteolytic cleavage of the full-length Oncostatin M, followed by truncation of the carboxy terminus at least one amino acid at a time. Up to all of the C-terminal portion of the molecule may be deleted from the full-length Oncostatin M. By "C-terminal portion" is intended amino acids 186 to 227 (FIG. 1).

Deletion mutants, processing mutants and substitution mutants of Oncostatin M may also be prepared by recombinant DNA techniques. Techniques used in isolating the Oncostatin M gene are known in the art, including synthesis, isolation from genomic DNA, preparation from cDNA, or combinations thereof. The various techniques for manipulation of DNA are well known, and include restriction, digestion, resection, ligation, in vitro mutagenesis, primer repair, and polylinkers and adapters, and the like. See, Maniatis et al., Molecular Cloning, Cold Spring Harbor Laboratory, Cold Spring Harbor, N.Y. (1982). Generally, the method comprises constructing and screening a cDNA library from cells which synthesize Oncostatin M, such as histiocytic lymphoma cells (U937) or PBL. An assay for either MRNA encoding Oncostatin M using a probe or assaying for the expression of Oncostatin M, then screening with antibodies for Oncostatin M to detect a cross-reactive peptide fragment or the like can be used.

Once a cDNA containing the Oncostatin M coding sequence has been identified, the desired modifications in the structural gene can be made in several ways. The modifications may involve deletions, insertions, combinations thereof, as well as substitutions, as described above. Changes, such as deletions, may involve the C-terminal region, particularly the region encoding amino acids 186 through the C-terminus.

Deletions may be made in a number of ways known to those skilled in the art, including by enzymatically cutting the full length Oncostatin M cDNA followed by modification and ligation of the purified fragments or by site-directed mutagenesis, especially by loop-out mutagenesis as described by Kramer et al., Nucl. Acids Res. (1984) 12: 9441–9456.

For purposes of the subject invention, the arious amino acids can be divided into a number of subclasses. The following table indicates the subclasses:

| aliphatic neutral | |
|---|---|
| non-polar | G A P V L I |
| polar | S T C M N Q |
| acidic | D E |
| basic | K R |
| aromatic | F H Y W |

By "conservative substitution," it is meant that amino acids from the same subclass (i.e., either neutral aliphatic, acidic aliphatic, basic aliphatic or aromatic), more particularly the same polarity, will be substituted from each other. Desirably, amino acids of two to four carbon atoms or five to six carbon atoms will define monomer groupings in the aliphatic subclass.

Higher molecular weight polypeptides may be prepared by joining one polypeptide fragment to a large immunogenic polypeptide carrier to provide for immunogenicity. Exemplary of such protein carriers are bovine serum albumin, keyhole limpet hemocyanin (KLH) and the like. Those conjugated polypeptides will be useful for inducing antibodies in an appropriate host organism. The antibodies can be used to determine the presence and/or concentration of Oncostatin M in a bodily fluid, the presence of which may further be used as a means of detecting the presence of a tumor cell, to bind to Oncostatin M and thus modulate its activity, and to purify Oncostatin M, as by use in an affinity column. The gene thus obtained may then be manipulated in a variety of ways well known in the art to provide for expression. Both prokaryotic and eukaryotic hosts may be employed, which may include bacteria, yeast, insect cells and mammalian cells, e.g., E. coli, COS cells, CHO cells, monkey kidney cells, and silkwork cells (sf9). Therefore, where the gene is to be expressed in a host which recognizes the wild-type transcriptional and translational regulatory regions of Oncostatin M, the entire gene with its wild-type 5'- and 3'-regulatory regions may be introduced into an appropriate expression vector. Various expression vectors exist employing replication systems from mammalian viruses, such as Simian Virus 40, adenovirus, bovine papilloma virus, vaccinia virus, insect baculovirus, etc. These replication systems have been developed to provide for markers which allow for selection of transfectants, as well as providing for convenient restriction sites into which the gene may be inserted.

Where the gene is to be expressed in a host which does not recognize the naturally occurring wild-type transcriptional and translational regulatory regions, further manipulation will be required. Conveniently, a variety of 3'-transcriptional regulatory regions are known and may be inserted downstream from the stop codons. The non-coding 5'-region upstream from the structural gene may be removed by endonuclease restriction, Bal31 resection, or the like. Alternatively, where a convenient restriction site is present near the 5'-terminus of the structural gene, the structural gene may be restricted and an adaptor employed for linking the structural gene to the promoter region, where the adaptor provides for the lost nucleotides of the structural gene.

Various strategies may be employed for providing for an expression cassette, which in the 5'-3'- direction of transcription has a transcriptional regulatory region and a translational initiation region, which may also include regulatory sequences allowing for the induction of regulation; the structural gene under the transcriptional and translational control of the initiation region; and translational and transcriptional termination regions. The expression cassette may additionally include leader sequences from bacteriophage or bacterial genes which provide for stability of the expression product, and secretory leader sequences which provide for secretion of the expression product, as well as marker genes.

The initiation and termination regions are functional in the host cell, and may be either homologous (derived from the original host), or heterologous (derived from a foreign source) or synthetic DNA sequences. The expression cassette thus may be wholly or partially derived from natural sources, and either wholly or partially derived from sources, and either wholly or partially derived from sources homologous to the host cell, or heterologous to the host cell. The various DNA constructs (DNA sequences, vectors, plasmids, expression cassettes) of the invention are isolated and/or purified, or synthesized and thus are not "naturally occurring".

For optimal gene expression, the nucleotide sequences surrounding the translational initiation codon ATG have been found to be important in animal cells. For example, Kozak, Microbiol. Reviews (1983) 47: 1–45, has studied extensively the effect of these regions on the expression of polypeptides such as insulin in COS cells. Thus it may be necessary to modify the nucleotide sequences surrounding the initiation codon. This can be done by site-directed mutagenesis or by fusing the exogenous gene to the initiation region of a highly expressed gene.

Illustrative transcriptional regulatory regions or promoters include, for bacteria, the β-gal promoter, lambda left and right promoters, trp and lac promoters, trp-lac fusion promoter, etc.; for yeast, glycolytic enzyme promoters, such as ADH-I and -II promoters, GPK promoter, and PGI promoter, TRP promoter, etc.; for mammalian cells, SV40 early and late promoters, adenovirus major late promoters, etc.

Where the transcriptional regulatory region additionally includes regulatory sequences which allow expression of the structural gene to be modulated, e.g., by presence or absence of nutrients or expression products in the growth medium, temperature, etc., the regulatory sequence may comprise the bacteriophage lambda $P_L$ promoter together with the bacteriophage lambda $O_L$ operator and the CI857 temperature-sensitive repressor, for example, to provide for temperature sensitive expression of the structural gene. Regulation of the promoter is achieved through interaction between the repressor and the operator.

In eukaryotic cells, regulatory sequences can include, for example, the cytomegalovirus enhancer sequence which can be fused to a promoter sequence such as the SV40 promoter, forming a chimeric promoter, or inserted elsewhere in the expression cassette, preferably in close proximity to the promoter sequence. Expression of the structural gene also can be amplified by, for example, ligating in tandem a gene for a dominant amplifiable genetic marker 5' or 3' to the structural gene and growing the host cells under selective conditions. An example of an amplifiable gene is the gene for dihydrofolate reductase (dhfr), expression of which may be increased in cells rendered resistant to methotrexate (mtx), a folate antagonist.

Of particular interest are expression cassettes capable of expressing Oncostatin M which employ the lac operator-promoter, the tac promoter, or the lambda $P_L$ promoter-$O_L$ operator, and a temperature-sensitive repressor, particularly in conjunction with the λ-Cro, lac or N-gene ribosome binding site. The structural gene is joined downstream from the ribosome binding site, so as to be under the regulatory control of the transcriptional regulatory region and the translational regulatory region. This is described in U.S. Ser. No. 264,098, filed Oct. 28, 1988, which disclosure is hereby incorporated by reference.

Stability of the expression product may be achieved by providing for synthesis of a fused protein comprising N-terminal amino acids from, for example, a bacteriophage lambda N-gene or Cro gene, or a bacteria alkaline phosphatase gene. The leader sequence is provided upstream from and in reading frame with the structural gene. The leader sequences of interest include from about 8 to about 35, preferably from about 15 to about 25 N-terminal amino acids from a prokaryotic gene, for example a bacteriophage lambda N-gene or Cro gene, or a bacterial alkaline phosphatase gene. See, for example, U.S. Ser. No. 264,098, filed Oct. 28, 1988.

In addition, a fused gene may be prepared by providing a 5'-sequence to the structural gene which encodes a secretory leader and processing signal. Illustrative secretory leaders include the secretory leaders of penicillinase, α-factor, immunoglobulins, T-cell receptors, outer membrane proteins, serum albumin, insulin, digestive tract enzymes, β-transforming growth factor and the like. By fusion in proper reading frame of the secretory leader with the structural gene, the mature Oncostatin M or analog may be secreted into the medium. See, for example, U.S. Ser. No. 144,574, filed Jan. 15, 1988, which disclosure is hereby incorporated by reference.

At least one additional amino acid may be inserted between the structural gene and the leader sequence, the intervening amino acid(s) providing for, for example, an enzymatic or chemical cleavage site for cleavage of the fusion protein. Alternatively, the fusion protein comprising the leader sequence and the stuctural gene product may find use without cleavage of the mature polypeptide.

The expression cassette may be included within a replication system for episomal maintenance in an appropriate cellular host or may be provided without a replication system, where it may become integrated into the host genome. The DNA may be introduced into the host in accordance with known techniques, such as transformation, transfection using calcium phosphate-precipitated DNA, electroporation, transfection with a recombinant virus, microinjection of the DNA into cells or the like.

Once the structural gene has been introduced into the appropriate host, the host may be grown to express the structural gene. The host cell may be grown to high density in an appropriate medium. Where the promoter is inducible, such as in a prokaryotic system, permissive conditions will then be employed, for example, temperature change, exhaustion, or excess of a metabolic product or nutrient, or the like. In a mammalian system, where an amplifiable gene is used in tandem with the structural gene, the appropriate means for amplification will be employed.

Where secretion is provided for, the expression product, either fused or unfused, may be isolated from the growth medium by conventional means. Where secretion is not provided for, the host cells may be harvested and lysed in accordance with conventional conditions. The desired product is then isolated and purified in accordance with known techniques, such as chromatography, electrophoresis, solvent extraction, or the like.

The recombinant products may be glycosylated or non-glycosylated, having the wild-type or other glycosylation. In general, the glycosylation will differ by not more than about 50% usually by not more than about 20% from the wild-type glycosylation. The amount of glycosylation will depend in part upon the sequence of the particular peptide, as well as the organism in which it is produced. Thus expression of the product in *E. coli* cells will result in an unglycosylated product, and expression of the product in insect cells generally will result in less glycosylation than expression of the product in mammalian cells.

5.1. USES OF ONCOSTATIN M MUTANTS AND ANALOGS

The Oncostatin M mutant and analog polypeptides, and compositions thereof, may be used for making antibodies, which may find use in vivo or in vitro. The antibodies may be prepared in conventional ways, either by using the subject polypeptide as an immunogen and injecting the polypeptide into a mammalian host, e.g., mouse, cow, goat, sheep, rabbit, etc., particularly with an adjuvant, e.g., complete Freunds adjuvant, aluminum hydroxide gel, or the like. The host may then be bled and the blood employed for isolation of polyclonal antibodies, or in the case of the mouse, the peripheral blood lymphocytes or splenic lymphocytes (B-cells) employed for fusion with an appropriate myeloma cell to immortalize the chromosomes for monoclonal expression of antibodies specific for the subject compounds. Either polyclonal or monoclonal antibodies may be prepared.

Oncostatin M mutants, analogs, and compositions thereof may be used as ligands for detecting the presence of Oncostatin M receptors. In this way, cells may be distinguished in accordance with the presence of and the density of receptors for Oncostatin M, monitoring the effect of various compounds on the presence of such receptors as well as determining the sensitivity of a given cell to the effects of a particular Oncostatin M mutant or analog. Additionally, peptides believed to have Oncostatin M-like biological activity may be evaluated by comparing their ability to bind to the Oncostatin M receptor with that of naturally occurring Oncostatin M. Generally, the test peptides can be evaluated by incubating the test peptide together with labeled Oncostatin M or another peptide which binds with high affinity to the Oncostatin M receptor with a preparation containing Oncostatin M receptors, and observing the amount of inhibition of binding of the labeled Oncostatin M, as described in the examples which follow. Evaluation of whether test peptides which bind to the receptor are Oncostatin M agonists or antagonists can then be determined by observing their effect on a biological function associated with Oncostatin M, for example, inhibition of growth of tumor cells, as described in the examples which follow.

Oncostatin M mutants, analogs and compositions thereof may be used in the treatment of a wide variety of neoplastic conditions, such as carcinomas, sarcomas, melanomas, lymphomas, leukemias, which may affect a wide variety of organs, such as the blood, lungs, mammary organ, prostate, intestine, liver, heart, skin, pancreas, brain, etc. They may be administered in vivo by injection, intralesionally, peritoneally, subcutaneously, or by any other appropriate route of administration. Administration may be in any physiologically acceptable carrier, such as sterilized water, phosphate buffered saline, saline, aqueous ethanol, etc. The subject compound may be used in vitro to eliminate malignant cells from marrow for autologous marrow transplants or to inhibit proliferation or eliminate malignant cells in other tissue, e.g., blood, prior to reinfusion. Also, the compositions can be used as antagonists for Oncostatin M induced growth stimulating activity of Kaposi's Sarcoma, or to stimulate DNA replication in ICS cells rendering them more sensitive to chemotherapeutic drugs.

Oncostatin M mutants, analogs and compositions thereof may also be used in the treatment of disorders of the hematopoietic system, especially as a means of stimulating hematopoiesis in patients with suppressed bone marrow function, for example, patients suffering from aplastic anemia, inherited or acquired immune deficiency, or patients undergoing radiotherapy or chemotherapy.

Oncostatin M mutants, analogs and compositions thereof also find use in the treatment of a wide variety of wounds including substantially all cutaneous wounds, corneal wounds, and injuries to the epithelial-lined hollow organs of the body. Wounds suitable for treatment include those resulting from trauma such as burns, abrasions, cuts, and the like as well as from surgical procedures such as surgical incisions and skin grafting. Other conditions suitable for treatment with the compositions of the present invention include chronic conditions, such as chronic ulcers, diabetic ulcers, and other non-healing (trophic) conditions. The subject compounds may be incorporated in physiologically-acceptable carriers for application to the affected area. The nature of the carriers may vary widely and will depend on the intended location of application. For application to the skin, a cream or ointment base is usually preferred, suitable bases include lanolin, Silvadene (Marion) (paricularly for the treatment of burns), Aquaphor (Duke Laboratories, South Norwalk, Conn.), and the like. If desired, it will be possible to incorporate Oncostatin M analog or mutant compositions in bandages and other wound dressings to provide for continuous exposure of the wound to the peptide. Aerosol applications may also find use.

The concentration of polypeptide in the treatment composition is not critical. The polypeptide will be present in an epithelial cell proliferation-inducing amount. The composition will be applied topically to the affected area, typically as eye drops to the eye or as creams, ointments or lotions to the skin. In the case of eyes, frequent treatment is desirable, usually being applied at intervals of 4 hours or less. On the skin, it is desirable to continually maintain the treatment composition on the affected area during healing, with applications of the treatment composition from two to four times a day or more frequently.

The subject compositions may be formulated in a variety of ways, including in the lumen of liposomes, particularly where the liposomes may be bound to homing molecules targeted for a particular neoplastic cells, e.g., antibodies, nondegradable particle matrices, or the like. Other components may be included in the formulation such as buffers, stabilizers, surfactants, biocides, etc. These components have found extensive exemplification in the literature and need not be described in particular here.

The results obtained in the following examples demonstrate that some mutant Oncostatin M polypeptides retain bioactivity, and in some cases possess enhanced bioactivity. Compositions comprising such mutants may be used in the regulation of cell proliferation both in vivo and in vitro, such as in culture, leucopheresis, propopylactic and therapeutic applications in vivo, etc. One particular application relates to the use of biologically active Oncostatin M mutant polypeptides to treat cells for autologous bone marrow transplants by inhibiting the growth of tumor cells in the marrow and by stimulating colony cell formation. Another specific application relates to the use of Oncostatin M mutants to stimulate the growth of epithelial cells thereby promoting wound healing. In addition, the mutant polypeptides may be used as immunogens to induce antibody formation. The induced antibodies may find use in titering the levels of Oncostatin M present in bodily fluids and/or to modulate the activity of the factor by binding to it.

Although the invention is described in some detail by way of illustration it will be readily apparent to those of ordinary skill in the art that certain changes and modifications may be made without departing from the spirit or scope of the appended claims. The following examples are offered by way of illustration and not by way of limitation.

6. EXAMPLE: EXPRESSION AND CHARACTERIZATION OF ONCOSTATIN M MUTANTS

6.1. MATERIALS AND METHODS
6.1.1. CELL CULTURE
A375 melanoma, H2981 and COS cells were cultured in Dulbecco's Modified Eagle's Medium (DMEM) supplemented with 10% fetal bovine serum (FBS).

6.1.2. GROWTH INHIBITION ASSAY
Growth inhibitory activity (GIA) was measured by a dye binding assay. A375 melanoma cells ($3-4 \times 10^3$) were seeded in a volume of 0.1 ml of DMEM containing 10% fetal bovine serum (FBS) in 96 well microtiter plates. Various concentrations of Oncostatin M were added in a volume of 0.1 ml, and incubation at 37° C. was continued for 72 hr. The culture medium was removed, cells were stained with crystal violet, and relative cell proliferation was quantitated by measuring bound dye on a microtiter plate reader (Genetic Systems Corp., Seattle, Wash.) by absorbance at 590 nm. Cellular proliferation in the presence of Oncostatin M was compared with proliferation in untreated samples, and is expressed as a percentage of inhibition of maximal growth. Samples were assayed in duplicate or triplicate. GIA units of Oncostatin M were determined from inhibition curves and are defined as the amount of protein neeeded to inhibit by 50% the growth of A375 cells in a standard assay. When GIA units were normalized for protein concentration, the coefficients of variation for the normalized values were generally <20%.

6.1.3. RADIORECEPTOR ASSAY
H2981 cells were seeded at a density of $1-3 \ 10^5/cm^2$ in 48 well plastic dishes 16–24 hours prior to treatment with Oncostatin M. Monolayers were incubated with $^{125}$I-Oncostatin M (20 ng/ml, 0.7 nM) in volume of 0.1 ml Binding Buffer (Linsley et al., 1986, Biochemistry 25: 2978–2986) containing increasing amounts of Oncostatin M or mutant Oncostatin M. Binding reactions were carried out for 2–4 hours at 23° C. Non-specific binding was measured in the presence of a 50- to 100-fold excess of unlabeled Oncostatin M. Specific binding was calculated by subtracting radioactivity bound in the presence of excess unlabeled Oncostatin M from total binding and generally ranged between 70%–95% of total binding. Variation between replicate determinations was generally less than 10%. Radioreceptor assay units (RRA units) were determined from inhibition curves obtained in the presence of increasing amounts of unlabeled Oncostatin M. One RRA unit is defined as the amount of Oncostatin M required for 50% inhibition of binding of $^{125}$I-Oncostatin M in a standard assay.

Specific activity values computed as GIA or RRA (unit/mg) varied between experiments by as much as two fold. Within an experiment, specific activity variations ranged from 15% to 30%, due in large part to the variation in quantifying the amount of immunoreactive protein in the culture media. Relative specific activity values indicate the percent specific activity of the mutant relative to that of recombinant "wild type" Oncostatin M. The derived coefficient of variation for relative specific activity ranged from 22% to 45%, calculated as root mean squared. Mutations resulting in relative specific activity values of less than 10% of recombinant "wild type" Oncostatin M are considered as having lost biological activity.

6.1.4. RADIOIMMUNOASSAY
Serum-free culture media was diluted in DMEM, dithiothreitol was added to a concentration of 10 mM, and proteins were denatured by boiling. This treatment increases the subsequent immunoreactivity of Oncostatin M. Serial dilutions of treated medium were then applied to a nitrocellulose membrane through a slot blot apparatus (Millipore). Membranes were then subjected to immunoblotting analysis as described (Linsley et al., 1985, Proc. Natl. Acad. Sci. (USA) 82: 356–360) using anti-6-19 antiserum (Section 6.1.5., infra) and $^{125}$I-protein A for detection. Standard curves were constructed using purified Oncostatin M diluted in serum-free medium from mock transfected cells. Band intensities on autoradiograms were measured by scanning desitometry, and the amount of Oncostatin M present in medium from transfected cells was quantified by comparison to standard curves. In most cases, the amounts of Oncostatin M measured in several dilutions of medium giving band intensities from the linear portion of the standard curve were averaged; the coefficients of variation of these measurements were generally <10%.

6.1.5. ANTISERA
Peptides corresponding to amino acids 6-19 and 206-218 of Oncostatin M (FIG. 1) were synthesized by solid phase techniques. Peptides were conjugated to bovine immunoglobulin (peptide 6-19) or keyhold limpet hemocyanin (peptide 206-218), and rabbits were immunized as described (Gentry et al., 1987, Mol. Cell. Biol. 7: 3418–3427; Linsley et al., 1985, Proc. Natl. Acad. Sci. USA 82: 356–360). For anti-6-19, a 1:1 mixture of sera from two immunized rabbits was used.

6.1.6. COS CELL TRANSFECTIONS
COS cells were transfected with Oncostatin M mutant-encoding plasmids as described (Malik, et al., 1989, Mol. Cell. Biol. 9: 2847–2853). Twenty-four hours following transfection, serum-free medium was added and cells were incubated at 37° C. for an additional 48 hours. Conditioned media was collected and assayed.

6.2. CONSTRUCTION OF EXPRESSION PLASMIDS

The Oncostatin M cDNA expression plasmid, pSPOM, is described in Malik, et al., 1989 Mol. Cell. Biol. 9: 2847–2853. An expression plasmid in which the sequence encoding Oncostatin M signal sequence is replaced with the sequence encoding the simian TGF-β1 signal peptide (herein referred to as pβ-OM) is described in Linsley et al., 1989, J. Biol. Chem. 264: 4282–89.

6.2.1. DELETION MUTANT CONSTRUCTS

Oncostatin M deletion mutants (stop condon insertion mutants) Δ182-227, Δ183-227, Δ184-227, Δ186-227, Δ187-227, Δ188-227, Δ189-227, Δ190-227, Δ195-227 and D196-227 were constructed by PCR amplification with 3' oligonucleotide primers encoding a stop codon and cloning site. Mutants Δ191 and Δ185 were constructed by limited exonuclease digestion (Henikoff, 1984 Gene 28: 351–359) from the 3' end of the Oncostatin M coding region. Briefly, the Oncostatin M CDNA was subcloned into the plasmid pSP64 (Promega), linearized near the 3' end of the cDNA, and subjected to limited digestion with exonuclease III. The 3' ends of the digested cDNAs were then blunted with Klenow fragment of DNA polymerase I. Finally, truncated cDNAs were excised from pSP64 at an engineered HindIII site 37 bases 5' to the translation start site and cloned into HindIII-XhoI cleaved πH3MPY (Stamenkovic, 1989, EMBO J.) using the synthetic oligonucleotide linkers TAGGTGAAT-GATCAC and TCGAGTGATCATTCACCTA, which encode for stop codons in each reading frame and have an overhanging end complementary to the XhoI restriction site. Individual clones having stop codons introduced at positions 183 and 190 (Δ183-227 and Δ190-227) were identified by DNA sequence analysis. Other deletion mutants were prepared similarly.

Several additional Oncostatin M deletion mutants (Δ44-47, Δ87-90, Δ118-121, Δ152-155 and Δ178-181) were constructed using the loop out deletion method (Kramer et al., supra). The mutant constructs were subcloned into the HindIII-XhoI site of pH3MPY, screened by restriction analysis and verified by sequencing the entire coding region.

6.2.2. PROCESSING MUTANTS CONSTRUCTS

Mutant clones G195 and G196 were constructed by oligonucleotide directed mutagenesis using a commercial kit (Amersham). Mismatched oligonucleotides directing the conversion of arginine residues at positions 195 or 196 into glycines were synthesized, and used as specified by the supplier to construct mutant clones. The sequence of the mutated region of clones G195 and G196 was confirmed by DNA sequence analysis.

Mutant clone G195 was constructed by a modification of the oligonucleotide mutagenisis procedure. Following repolymerization and ligation of gapped M13 phage DNA, Oncostatin M cDNA was amplified using Tac polymerase chain reaction (Perkin Elmer Cetus), using M13 universal forward and reverse primers. The amplified cDNA was then subcloned into HindIII-XhoI cleaved pH3MPY, and mutant clones were identified by restriction analysis and/or DNA sequencing. The mutated coding regions were then confirmed by sequence analysis. Sequence analysis of G195 revealed that the second amino acid of Oncostatin M (Alanine) had been exchanged for Valine as a result of a secondary mutation introduced during mutagenesis. G196 was purified by two cycles of a two step procedure consisting of an initial reversed phase chromatography step, followed by size fractionation.

6.2.3. SUBSTITUTION MUTANT CONSTRUCTS

Mutant clones S5, S49, S80, S127 S167 and S6/S167 were constructed by oligonucleotide mutagenesis as described in Section 6.2.2., supra. Mismatched oligonucleotides directing the conversion of cysteines at positions 6, 49, 80, 127, 167, and 6+167 were synthesized and used to construct mutant clones. Mutant constructs were subcloned into the HindIII-XhoI site of pH3MPY. The mutated coding regions of the resulting clones were confirmed by DNA sequence analysis.

6.2.4. INSERTION MUTANTS CONSTRUCTS

Mutant clones GAG6, GAG77, GAG14 and GAG140 were constructed by oligonucleotide directed in vitro mutagenesis as described in Section 6.2.2., supra. Mutant constructs were subcloned into the HindIII-XhoI site of pH3MPY. The mutated coding regions were confirmed by DNA sequence analysis.

6.3. BIOACTIVITY OF ONCOSTATIN M MUTANTS

6.3.1. DELETION AND PROCESSING MUTANTS

Serum-free media from COS cells transfected with plasmids encoding processing mutants G195 and G196 (Section 6.2.2., supra) and deletion mutants Δ195 and Δ190 (Section 6.2.1., supra) clones were analyzed by immunoblotting analysis.

Cells transfected with these mutant-encoding constructs produced proteins which reacted with anti-6-19 serum. Immunoreactive proteins produced by G195 and G196 comigrated with the $M_r36,000$ protein from pSPOM transfected cells (Section 7, infra), while Δ195 and Δ190 produced proteins which migrated more closely to the $M_r32,000$ protein. When anti-208-219 serum was used for analysis, the $M_r36,000$ form from G195 and G196 transfected cells was observed, but the Δ195 and Δ190 produced proteins failed to react. Thus, introduction of point mutations at a putative processing site prevented accumulation of the $M_r32,000$ form, while deletion mutations just upstream of this site prevented accumulation of the $M_r36,000$ form of Oncostatin M. These results suggest that the difference between the $M_r36,000$ and $M_r32,000$ forms of Oncostatin M is due to proteolytic processing at or near the tryptic-like site beginning at position 193.

The biological activity of the processing-resistant mutant forms of Oncostatin M (G195 and G196) with mutant proteins closely corresponding in size to the $M_r32,000$ form of Oncostatin M (Δ190 and Δ182) were compared. For this experiment, untreated serum-free conditioned media from transfected cells were tested for GIA and RRA activities as described in Section 6.1.2. and 6.1.3., respectively. Oncostatin M concentrations were determined by radioimmunoassay as described in Section 6.1.4. As shown in Table I, the ratios of GIA to RRA activities for Δ190 and Δ195 were 10–20 fold higher than those of G195 and G196. Medium from cells transfected with mutant Δ182 gave no significant activity in either assay, indicating that the C-terminal region from residue 182–190 was essential for both growth inhibitory and binding activities. Medium from pSPOM (Section 7, infra) transfected cells gave intermediate activity ratios, consistent with the presence in this sample of two forms of Oncostatin M having different activities. These observations indicate that mutant unprocessed forms of Oncostatin M (G195 and G196) have less GIA activity than truncated $M_r32,000$ forms (Δ182 and Δ190).

TABLE I

MUTANT FORMS OF ONCOSTATIN M HAVE DIFFERENT RELATIVE GROWTH INHIBITORY AND BINDING ACTIVITIES

| SAMPLE | GIA ACTIVITY[1] | | RRA ACTIVITY[1] | | RATIO[2] |
|---|---|---|---|---|---|
| pSPOM | 11.7 | (27.2) | 2.6 | (6.1) | 4.5 |
| Δ195–227 | 61.7 | (74.3) | 3.2 | (3.8) | 19.5 |
| Δ190–227 | 20.0 | (21.7) | 0.9 | (1.0) | 22.5 |
| Δ182–227 | 0.02 | (0.06) | <0.02 | (<0.06) | N/A |
| G196 | 6.6 | (8.0) | 11.2 | (13.5) | 0.6 |
| G195 | 5.0 | (8.8) | 5.3 | (9.3) | 0.9 |

TABLE I-continued

MUTANT FORMS OF ONCOSTATIN M HAVE DIFFERENT
RELATIVE GROWTH INHIBITORY AND BINDING ACTIVITIES

| SAMPLE | GIA ACTIVITY[1] | RRA ACTIVITY[1] | RATIO[2] |
|---|---|---|---|

Untreated serum-free media from COS cells transfected
with the indicated plasmids were tested for growth inhibitory (GIA) and radioreceptor (RRA) activities as described
in Example 1. Oncostatin M concentrations were determined
by radioimmnoassay as described in Example 1; the concentrations ranged from 0.4–1 µg/ml. N/A, not applicable.

[1]Units/ml (×10³); numbers in parenthesis represent specific activities.
[2]Ratio GIA activity to RRA activity.

To confirm the reduced GIA activity of the G196 mutant, this protein was purified to homogeneity and compared to the $M_r$32,000 form of Oncostatin M from pSPOM transfected cells (Section 7, infra). The purified $M_r$32,000 form of Oncostatin M had greater GIA activity than G196 (half-maximal activities at 6 and 130 pM, respectively). In three separate experiments, the difference in growth inhibitory activities between these purified proteins was 9-fold, 22-fold and 5-fold (mean±standard deviation (12±9-fold)). In contrast, RRA, activities of the two purified proteins were indistinguishable (half-maximal activities of approximately 100 pM). In the RRA, three separate experiments showed that G196 had approximately 1.1, 1.1 and 2-fold greater (1.3±0.3-fold) RRA activity than the $M_r$32,000 form of Oncostatin M. Thus, purified G196 ($M_r$36,000 form) binds to the Oncostatin M receptor equally as well as the $M_r$32,000 form, but has less GIA activity.

Figure 2:
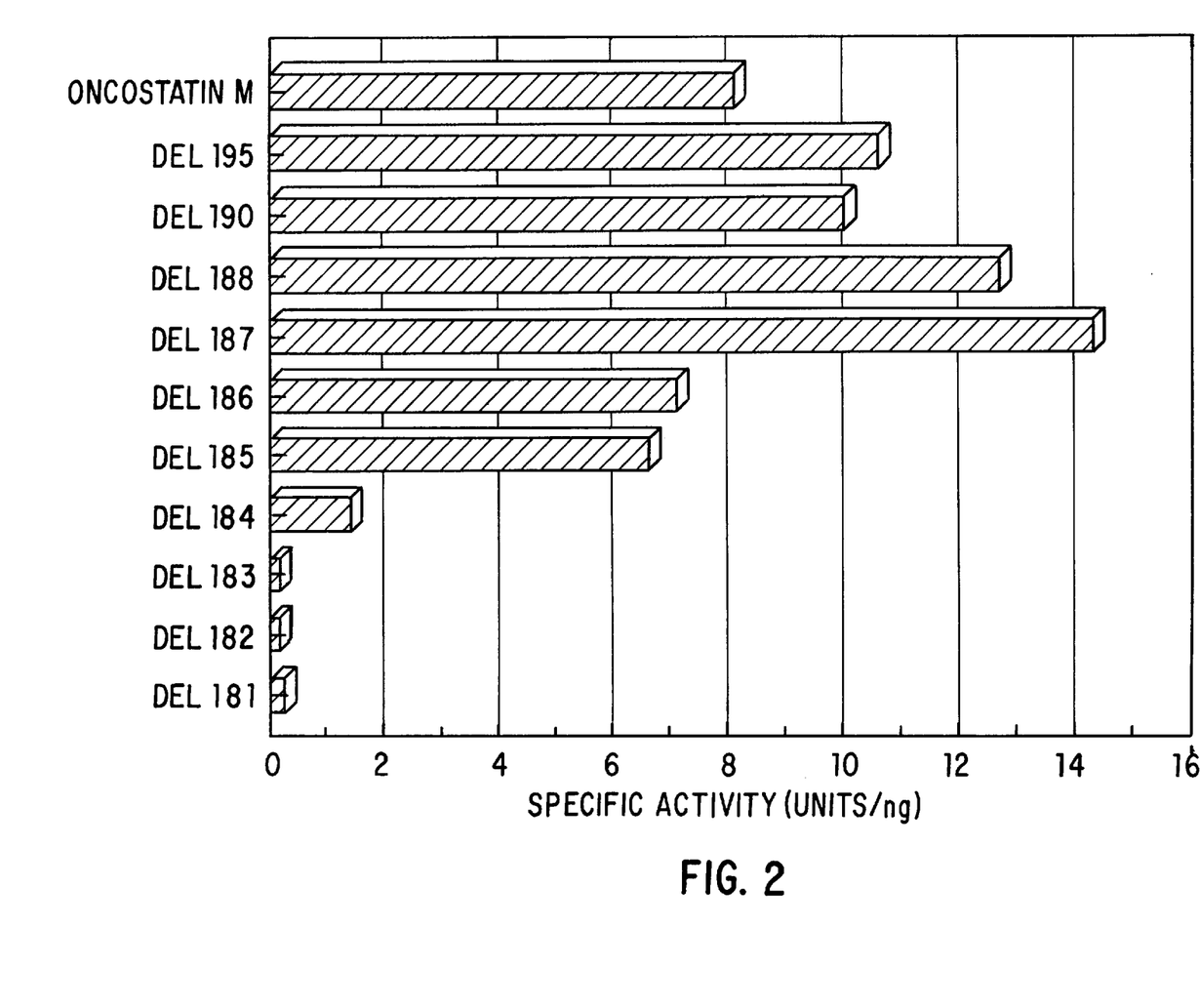
FIG. 2. Growth inhibitory activity of C-terminal deletion Oncostatin M mutants.

A comparison of the growth inhibitory activities of Oncostatin M deletion mutants is shown in FIG. 2. Δ181, Δ182, and Δ183 have minimal growth inhibitory activity (<1 Unit/ng). Enhanced growth inhibitory activity relative to native Oncostatin M was observed with the Δ195-227, Δ190-227, Δ188-227, and Δ187-227 Oncostatin M mutants. Mutant Δ187-227 exhibited the highest activity (>14 Units/ng) in comparison to native Oncostatin M (~8 Units/ng). Thus, removal of substantial portions of the C-terminal region increases the growth inhibitory activity of Oncostatin M.

Table II presents relative specific growth inhibitory and receptor binding activities of several Oncostatin M deletion mutants. This data confirms that the removal of substantial portions of the C-terminal region increases the growth inhibitory activity of Oncostatin M.

TABLE II

RELATIVE GROWTH INHIBITORY AND RECEPTOR BINDING
ACTIVITIES RESULTING FROM MUTATIONS AT THE
C-TERMINUS

| | RELATIVE SPECIFIC ACTIVITY (%) | | |
|---|---|---|---|
| MUTANT | GIA | RRA | n |
| Δ196–227 | 171 | 73 | |
| Δ191–227 | 90 ± 30 | 26 ± 13 | 3 |
| Δ190–227 | 99 | 68 | |
| Δ189–227 | 197 ± 57 | 42 ± 1 | 2 |
| Δ188–227 | 135 | 54 | |
| Δ187–227 | 66 ± 31 | 21 ± 5 | 2 |
| Δ186–227 | 60 ± 30 | 20 ± 4 | 2 |
| Δ185–227 | 17 | 2 | |
| Δ184–227 | 2 | <1 | |
| Δ183–227 | <2 | <1 | 2 |
| Δ182–227 | <3 | <1 | 2 |

TABLE II-continued

RELATIVE GROWTH INHIBITORY AND RECEPTOR BINDING
ACTIVITIES RESULTING FROM MUTATIONS AT THE
C-TERMINUS

| | RELATIVE SPECIFIC ACTIVITY (%) | | |
|---|---|---|---|
| MUTANT | GIA | RRA | n |

Serum-free media from COS cells transfected with the inidcated Oncostatin M mutants were tested for growth inhibitory (GIA) and radioreceptor (RRA) activities. Oncostatin M concentrations were determined by quantitative immunoblotting, and ranged from 0.2–1.0 µg/ml. Values indicate the percent specific activity of the mutants relative to wild type recombinant Oncostatin M tested in the same experiment and calculated as specific activity of the mutant/specific activity of wild type Oncostatin M × 100. The number of experiments is indicated by "n".

6.3.2. SUBSTITUTION MUTANTS

Figure 3:
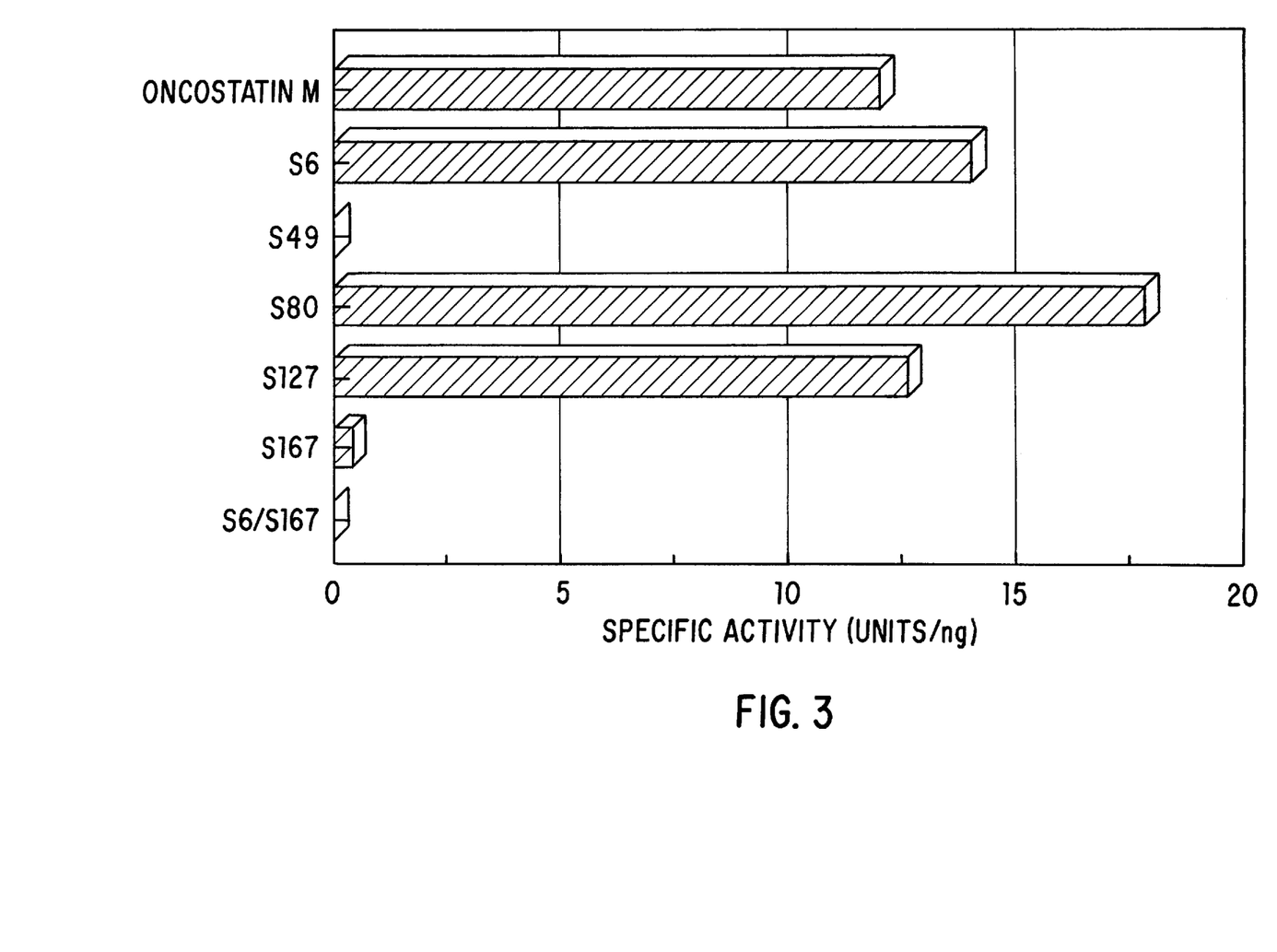
FIG. 3. Growth inhbitory activity of cysteine to serine Oncostatin M mutants.

Mutant clones prepared as described in Section 6.2.3., supra, were tested for growth inhibitory activity. The results presented in FIG. 3 demonstrate that the cysteines at positions 49 and 167 are essential for biological activity, as all mutants lacking these residues (S49, S167 and S6/167) had minimal or no biological activity. Substitution mutants S6, S80 and S127 had biological activities equivalent to or greater than the activity of native Oncostatin M, results which indicate that the cysteines at positions 6, 80, and 127 are not essential for Oncostatin M GIA. In fact, changing the cysteine at position 80 to serine resulted in a slight but significant increase in bioactivity.

6.3.3. ONCOSTATIN M MUTATIONS INVOLVING DELETIONS AND INSERTIONS OF AMINO ACIDS

Scanning deletion and insertion mutants were prepared as described in Sections 6.2.1., and 6.2.4., respectively, and were tested for growth inhibitory and radioreceptor activities (Table III). Deletion mutants Δ22-36 and Δ44-47 lost all GIA and RRA activities, while mutant Δ87–90 had higher relative specific activity than wild type Oncostatin M. Deletion mutant Δ152-155 had intermediate relative specific activity. Insertion of Gly-Ala-Gly between amino acid positions 5 and 6, 103 and 104, and 139 and 140 resulted in no significant loss in biological activity. Relative specific GIA and RRA activities were significantly reduced when the insertion of the Gly-Ala-Gly sequence was between amino acid positions 76 and 77, the putative N-linked glycosylation recognition sequence beginning at amino acid position 75.

TABLE III

RELATIVE SPECIFIC GROWTH INHIBITORY AND
RECEPTOR BINDING ACTIVITIES RESULTING FROM
SCANNING DELETION AND INSERTION MUTATIONS

| | RELATIVE SPECIFIC ACTIVITY (%) | |
|---|---|---|
| MUTANT | GIA | RRA |
| Δ22–36 | <1 | <5 |
| Δ44–47 | <1 | <3 |
| Δ87–90 | 320 | 260 |
| Δ152–155 | 39 | 48 |
| GAG6 | 58 | 37 |
| GAG77 | 8 | 24 |
| GAG104 | 125 | 196 |
| GAG140 | 79 | 40 |

Serum-free media from COS cells transfected with the indicated Oncostatin M mutant constructs (deletion of residues including those numbered shown as "Δ", and insertion of Gly-Ala-Gly residues at noted positions are

TABLE III-continued

RELATIVE SPECIFIC GROWTH INHIBITORY AND
RECEPTOR BINDING ACTIVITIES RESULTING FROM
SCANNING DELETION AND INSERTION MUTATIONS
RELATIVE SPECIFIC ACTIVITY (%)

| MUTANT | GIA | RRA |
|---|---|---| shown as "GAG") were tested for growth inhibitory (GIA) and radioreceptor (RRA) activities. Oncostatin M concentrations were determined by quantitative immunoblotting, and ranged from 0.14 to 1.8 μg/ml. Values indicate the percent specific activity of the mutant relative to wild type recombinant Oncostatin M tested in the same experiment, calculated as specific activity of the mutant/specific activity of wild type Oncostatin M × 100.

7. EXAMPLE: EXPRESSION OF ONCOSTATIN M IN COS CELLS GENERATES TWO MOLECULAR FORMS

7.1. COS TRANSFECTIONS

COS cells were transfected with pSPOM or pβOM as described (Malik, et al., 1989 Mol. Cell. Biol. 9: 2847–2853). Twenty-four hours following transfection, serum-free medium was added and cells were incubated at 37° C. for an additional 48 hours. Conditioned media was collected, and assayed immediately or acidified by addition of acetic acid to 1N, and concentrated for purification. Medium from the cells transfected with pSPOM contained two proteins ($M_r 36,000$ and $M_r 32,000$) which were immunologically related, but not identical in size, to native Oncostatin M made by U937 cells. These same proteins were also observed when COS cells were transfected with a construct encoding Oncostatin M having its signal sequence replaced with signal peptide from simian TGF-β1 (pβOM) N-terminal amino acid sequencing of both the $M_r 36,000$ and $M_r 32,000$ proteins revealed the same N-terminal sequence as natural Oncostatin M, indicating that the difference between these proteins is not a consequence of N-terminal sequence heterogeneity.

7.2. PURIFICATION OF THE $M_r 32,000$ FORM OF ONCOSTATIN M

The $M_r 32,000$ form of Oncostatin M was purified essentially as described (Linsley, et al., and Malik, et al., supra) from acidified and concentrated serum-free medium from COS cells transfected with pSPOM. Peak fractions of growth inhibitory activity from size-fractionated culture medium were collected and subjected to final purification by reversed phase chromatography. The resulting preparations contained predominantly the $M_r 32,000$ form of Oncostatin M. In some experiments, the Oncostatin M used for radiolabeling with $^{125}I$ or for standard curves in the radioimmunoassay was prepared in identical fashion from serum-free medium of CHO cells which overproduce recombinant Oncostatin M (Oncogen; Seattle, Wash.). Oncostatin M from this purified source does not show immunoreactivity with anti-206-218 antiserum and has properties equivalent to the $M_r 32,000$ form of Oncostatin M from COS cells.

7.3. $M_r 36,000$ FORMS

The $M_r 36,000$ form of Oncostatin M from pSPOM transfected cells was partially purified in a three-step procedure. Serum-free culture medium was acidified and size-fractionated on a TSK 3000SW column run in 40% acetonitrile, 0.1% trifluoracetic acid. Fractions containing predominantly the $M_r 36,000$ form of Oncostatin M were identified by immunoblotting analysis using anti-6-9 serum, pooled, concentrated and re-run over the same column. Fractions containing immunochemically pure $M_r 36,000$ form (i.e., having no detectable $M_r 32,000$ form) were pooled and used for subsequent experiments. Concentrations of purified proteins were determined by amino acid analysis performed by Dr. Gary Hathaway (Biotechnology Instrumentation Center, University of California, Riverside).

7.4. ELECTROPHORESIS

Sodium dodecyl sulfate polyacrylamide gel electrophoresis (SDS-PAGE) was performed using the Laemmli system (Laemmli, U. K., Nature (1970) 227: 680–685). Linear acrylamide gradient gels with stacking gels of 5% acrylamide were used. Samples were run under reducing conditions. Gels were stained with silver reagent (BioRad) or Coomassie Blue, destained, and dried before being photographed. The apparent molecular weights of the different forms of Oncostatin M were calculated by comparison with standards as described (Malik, et al., supra).

7.5. TRYPSIN TREATMENT OF $M_r 36,000$ ONCOSTATIN M

The $M_r 36,000$ form of Oncostatin M was partially purified by size fractionation and subjected to further purification by reversed phase chromatography. The resulting preparation was ~80% pure as judged by SDS-PAGE. Aliquots containing ~150 ng Oncostatin M (estimated by RRA) were treated at 37° C. with 6 ng TPCK-treated trypsin (Worthington) in 30 μl of 50 mM Tris acetate, pH 7.9. Samples were incubated at 37° C. for increasing lengths of time, reactions were terminated by addition of concentrated electrophoresis sample buffer, and different forms of Oncostatin M were identified by immunoblotting with anti-6-19 serum.

7.6. REMOVAL OF OLIGOSACCHARIDES

The predicted Oncostatin M precursor sequence contains two potential N-linked glycosylation sites. To determine whether differential glycosylation at these sites could account for the difference in the $M_r 36,000$ and $M_r 32,000$ forms of Oncostatin M, proteins present in serum-free conditioned medium from COS cells transfected with pSPOM were treated with the enzyme N-glycanase, which removes N-linked oligosaccharides, and analyzed for immunoreactivity with a site-specific anti-sera to Oncostatin M (anti-6-19). Mobilities of both the $M_r 36,000$ and $M_r 32,000$ forms of Oncostatin M were increased by this treatment, resulting in new species of $M_r \sim 34,000$ and $M_r 30,000$. The increase in mobility of both fragments is consistent with the removal of one N-linked oligosaccharide moeity ($M_r \sim 2,000$) from each form of Oncostatin M. Since mobilities of both forms were increased in parallel, it is unlikely that differential N-linked glycosylation could account for the size difference between these fragments.

7.7. SITE-SPECIFIC ANTISERA REVEAL DIFFERENT C-TERMINI FOR THE $M_r 36,000$ AND $M_r 32,000$ FORMS OF ONCOSTATIN M

Hydropathy analysis (Keski-Oji, J. et al., J. Cell. Biochem. Suppl. (1987) 11A: 60) revealed that the C-terminus of Oncostatin M (amino acids ~190-227) is strongly hydrophilic. Basic amino acids (R, K, or H) comprise 24 of 38

(63%) of the residues in this region, and there are five paired dibasic residues which could represent potential proteolytic cleavage sites. To invesitgate whether C-terminal heterogeneity accounts for the difference between the $M_r36,000$ and $M_r32,000$ forms, antisera were raised to peptides corresponding to regions from the N-terminus of mature Oncostatin M (Malik, et al., supra and Zarling, J. M. et al., 1986, Proc. Natl. Acad. Sci. 83: 9739–9743) and the C-terminus predicted from the cDNA sequence. These antisera were then used in immunoblotting experiments with serum-free conditioned medium from pSPOM transfected cells and natural U937 cell-derived Oncostatin M. While anti-6-19 serum reacted with both the $M_r36,000$ and $M_r32,000$ forms from pSPOM transfected cells, and with $M_r28,000$ natural Oncostatin M from U937 cells, anti-206-218 serum reacted only with the $M_r36,000$ form of Oncostatin M. The specificity of both antisera was indicated by the ability of the cognate peptides to inhibit their reactivities. These results indicate that differences between the $M_r36,000$ and $M_r32,000$ forms of Oncostatin M can be accounted for, at least in part, by C-terminal heterogeneity which presumably results from proteolytic processing within the hydrophilic C-terminal domain.

7.8. CONVERSION OF THE $M_r36,000$ FORM OF ONCOSTATIN M TO THE $M_r32,000$ FORM BY LIMITED PROTEOLYSIS

To confirm that proteolytic processing of the $M_r36,000$ form of Oncostatin M gives rise to the $M_r32,000$ form, a partially purified preparation of the $M_r36,000$ form was subjected to limited proteolysis. Reaction products were detected with anti-6-19 serum. With increasing time of trypsinization, a gradual decrease in the amount of the $M_r36,000$ form of Oncostatin M was seen, concomitant with an increase in the amount of the $M_r32,000$ form. At the longest time point tested, the amount of $M_r32,000$ form was decreased and additional immunoreactive products of lower molecular weight were observed. Since the $M_r32,000$ product reacts with N-terminal specific antiserum, it represents Oncostatin M which has been processed at the C-terminus. This indicates that proteolysis near the C-terminus of the $M_r36,000$ form of Oncostatin M can give rise to a form of Oncostatin M similar in size to the $M_r32,000$ form produced by cells transfected with pSPOM.

7.9. GROWTH INHIBITORY ACTIVITY OF ONCOSTATIN M (32K AND 36K FORMS)

Serum-free conditioned medium from pβOM transfected cells was fractionated by chromatography over BioGel P60. Individual fractions were then tested for GIA activity on A375 melanoma cells and tested for immunoreactivity with anti-6-19. Peak fractions fo GIA activity eluted between fractions 35 and 40, well behind the bulk of $A_{280}$ absorbing material. The precise peak fraction of GIA activity could not be determined in this experiment because peak fractions contained more activity than could be accurately measured at the dilutions tested.

Immunoblotting analysis indicated that the $M_r32,000$ form of Oncostatin M eluted with fractions containnig the bulk of GIA activity. In contrast, the $M_r36,000$ form eluted several fractions ahead (peak in fraction 33) of the main peak of GIA activity. Since fractions containing the $M_r36,000$ form stained more intensely, but had less GIA activity than the $M_r32,000$ form, the specific GIA activity of the $M_r36,000$ form appears to be less than that of the $M_r32,000$ form.

To make quantitative comparisons of biological activities of the $M_r32,000$ and $M_r36,000$ forms, size fractionated fractions containing predominantly one form or the other were pooled and compared for both GIA and RRA activities. For this analysis, a different column (TSK 3000SW) was used which gave qualitatively similar results to BioGel P60, but offered better separation between the $M_r36,000$ and $M_r32,000$ forms. Pooled fractions were analyzed by immunoblotting to confirm the lack of cross-contamination with the alternate form of Oncostatin M. Analysis of stained gels followed SDS-PAGE indicated that the purity of each form of Oncostatin M was approximately 20% for the $M_r36,000$ form and 80% for the $M_r32,000$ form. As shown in Table IV, partially purified $M_r36,000$ had less GIA activity, but more RRA activity than the $M_r32,000$ form. This difference is apparent in the approximately 10-fold greater ratio between these activities for the $M_r32,000$ than the $M_r36,000$ form.

TABLE IV

| SAMPLE | GIA ACTIVITY[1] | RRA ACTIVITY[1] | RATIO[2] |
| --- | --- | --- | --- |
| 36K form | 104 | 43.5 | 2.4 |
| 32K form | 345 | 17.9 | 19.2 |

Fractions containing the M 36,000 or M 32,000 forms were pooled, and aliquots were tested for growth inhibitory (GIA) and radioreceptor (RRA) activities.

[1]Units/ml ($\times 10^{-3}$).
[2]Ratio of GIA activity to RRA Activity.

What is claimed:

1. An oncostatin M mutant comprising the amino acid sequence as depicted in FIG. 1 wherein any of the amino acids from and including the residue at position 186 to and including the carboxyl-terminal residue at position 227 are deleted.

2. The Oncostatin M mutant according to claim 1 wherein amino acids 186 through 227 are deleted.

3. The Oncostatin M mutant according to claim 1 wherein amino acids 196 through 227 are deleted.

4. The Oncostatin M mutant according to claim 1 wherein amino acids 189 through 227 are deleted.

5. The Oncostatin M mutant according to claim 1 wherein amino acids 188 through 227 are deleted.

6. An oncostatin M mutant comprising the amino acid sequence as depicted in FIG. 1 wherein any of the amino acid at positions 6, 80 and 127 are substituted by an amino acid other than cysteine.

7. The Oncostatin M mutant according to claim 6 wherein the substituted amino acid is serine.

8. An oncostatin M mutant comprising the amino acid sequence as depicted in FIG. 1 wherein amino acids 87 through 90 are deleted.

9. An oncostatin M mutant comprising the amino acid sequence as depicted in FIG. 1 wherein amino acids 152 through 155 are deleted.

10. An oncostatin M mutant comprising the amino acid sequence as depicted in FIG. 1 wherein any of the amino acids at positions 195 and 196 are substituted by an amino acid other than arginine.

11. The Oncostatin M mutant according to claim 10 wherein the substituted amino acid is glycine.

12. An oncostatin M mutant comprising the amino acid sequence as depicted in FIG. 1 wherein the amino acid sequence GAG is inserted between amino acids 103 and 104.

* * * * *